(12) United States Patent
Burkhead et al.

(10) Patent No.: US 6,296,641 B2
(45) Date of Patent: *Oct. 2, 2001

(54) ANATOMICAL FIXATION IMPLANT

(75) Inventors: W. Burkhead, Dallas, TX (US); Pertti Törmälä, Tampere (FI); Harri Happonen, Tampere (FI); Pertti Helevirta, Tampere (FI); Auvo Kaikkonen, Tampere (FI); Timo Pohjonen, Tampere (FI)

(73) Assignee: Bionx Implants Oy, Tampere (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/055,005

(22) Filed: Apr. 3, 1998

(51) Int. Cl.[7] .................................................. A61B 17/56
(52) U.S. Cl. ............................................ 606/61; 606/213
(58) Field of Search ................................ 606/61, 62, 71, 606/72, 74–77, 105, 219, 220, 139, 140, 232, 213

(56) References Cited

U.S. PATENT DOCUMENTS

| | | |
|---|---|---|
| 4,503,847 | 3/1985 | Mouradian . |
| 5,246,441 * | 9/1993 | Ross et al. ............................ 606/53 |
| 5,259,398 | 11/1993 | Vrespa . |
| 5,454,814 * | 10/1995 | Comte ................................... 606/75 |
| 5,601,558 * | 2/1997 | Torrie et al. .......................... 606/72 |
| 5,634,926 | 6/1997 | Jobe . |
| 5,843,084 * | 12/1998 | Hart et al. ............................. 606/77 |
| 5,941,881 * | 8/1999 | Barnes ................................... 606/71 |
| 6,015,410 * | 1/2000 | Tormala et al. ....................... 606/73 |

* cited by examiner

Primary Examiner—Henry J. Recla
Assistant Examiner—Lien Ngo
(74) Attorney, Agent, or Firm—Kenyon & Kenyon (57) ABSTRACT

A fixation implant generally includes at least one shaft configured to securely fit into a hole formed in bone. The shaft is of sufficient length relative to the interior diameter of the hole and, in some preferred embodiments, has locking protuberances, like threads, ridges, or barbs, that resist removal of the shaft from the hole in the bone when different types of forces, such as tensile or bending forces, are applied to the implant. The shaft is generally cylindrical in shape, however, in various embodiments, different cross-sections could be used. In a preferred embodiment the implant has a flattened and bent end portion emerging from only one side of the shaft. At the other side of the implant the outer surface of the shaft and the emerging end portion form a smooth surface, without any projections. This smooth surface at the end of the implant prevents irritation of the surrounding tissue. The end portion has a mating surface configured to grip a portion of the soft tissue surrounding the hole between the bone and the mating surface. The longitudinal axis of the shaft is oriented at an angle of less than 90 degrees relative to the mating surface. In this fashion, the implant anchors soft tissue, such as rotator cuff tissue, to bone.

15 Claims, 6 Drawing Sheets

ANATOMICAL FIXATION IMPLANT

BRIEF DESCRIPTION OF THE INVENTION

This invention relates in general to a bioabsorbable surgical tissue fixation implant (nail) and, more particularly to an implant for the fixation of soft tissue to bone.

In such procedures as rotator cuff surgery or labrum rupture fixation surgery and hand tendon surgery, tendons or other soft tissues are fixed to bone. The tendons or other tissue are often secured to bone by feeding the soft tissue through holes formed in the bone and suturing the tissue in place. Another method of securing soft tissue to bone employs a fixation device which essentially tacks the tendon to bone. Unless the tendon or other soft tissue is completely immobilized, the fixation device must be securely embedded in the bone to hold the tendon or other soft tissue stationary against the bone surface, resisting those forces tending to pull the tendon or soft tissue away from the bone surface, until the tendon or soft tissue has become attached to the bone. Another method of securing tendon and other soft tissue to bone uses a fixation device (suture anchor) with an attached suture. Once again, the fixation device must be securely embedded in bone to resist forces tending to pull the tissue away from the bone surface.

Bioabsorbable soft-tissue fixation devices are frequently used, because they biodegrade after the tissue has healed and therefore do not cause long-term problems in the tissue and do not require a removal operation.

However, the presently known bioabsorbable fixation implants for attaching soft tissue to bone have encountered several problems in clinical use, especially in rotator cuff or labrum rupture fixation. According to references E. E. Berg and W. Oglesby, J. Shoulder & Elbow Surg. 5, pp. 76–78 (1996) and P. Kavli et al. Acta Orthop. Scand. 272, p. 24 (1996), the entire disclosures of which are incorporated herein by reference, the use of bioabsorbable tacks and staples in the surgical fixation of shoulder instability led to recurrent instability or loosening, causing healing problems. Bioabsorbable nails or bolt-type tacks, which are stronger than staples, have symmetrical heads that are anatomically unsuitable to labrum or rotator cuff fixation as can be seen from schematic FIG. 1. The symmetrical head of the tack does not mate effectively with the bone surface because the angle between the tack head and the shaft is 90 degrees, while the angle between the bone surface and the shaft is less than 90 degrees. Additionally, that part of the symmetric head (on the right side of the shaft in FIG. 1) which does not bind the soft tissue, is unnecessary for healing and can irritate the rim of the joint cavity.

U.S. Pat. No. 5,634,926, the entire disclosure of which is incorporated herein by reference, describes a bone or soft tissue fixation implant having a leg (shaft) portion and an enlarged end (head) portion arranged so that the longitudinal axis of leg portion being oriented at an angle of 15 to 55 degrees relative to the mating surface of the enlarged end. However, this implant is expressly restricted to those applications where no forces will be exerted on the implant that will tend to pull it out of the bone. This implant does not effectively grip the drill hole in the bone to resist tensile forces, because the leg portion is constructed so that it is easily pulled in a direction parallel to the longitudinal axis of said hole. Therefore, the high muscular forces which load the labrum or rotator cuff during healing would pull the leg portion at least partially from the drill hole during healing, causing severe complications.

Another problematic feature of the implant of U.S. Pat. No. 5,634,926 is that the enlarged end, even if non-symmetrical, still projects in all directions from the leg portion. Thus, the portion of the end that is directed to the rim of the joint cavity in labrum or rotator cuff fixation is ineffective and unnecessary for soft tissue fixation and can cause irritation to the rim of the joint cavity.

Accordingly, there is a need for a bioabsorbable fixation implant that is capable of securely and effectively affixing ruptured rotator cuff or labrum tissue to the bone and/or cartilage surface and is designed to optimize fixation capacity and to avoid unnecessary mass and mechanical irritations of shoulder joint tissues.

OBJECTS AND SUMMARY OF THE INVENTION

It is a primary object of this invention to provide a fixation implant for the effective surgical fixation of soft tissue or tendon tissue to bone.

It is another object of this invention to provide a fixation implant for the fixation of rotator cuff or labrum tissue to bone and/or cartilage surface in which the size of the fixation implant is minimized.

It is further an object of this invention to provide a fixation implant which may be fabricated of materials which are absorbed by the body over time.

It is further an object of this invention to provide a fixation implant which may be economically manufactured and which may be efficiently and reliably employed in the fixation of soft tissue to bone.

In summary, this invention provides a fixation implant that is particularly suitable for use in the fixation of soft tissue to bone. In one embodiment of the invention, the fixation implant generally includes at least one shaft configured to securely fit into a hole formed in bone. The shaft is of sufficient length relative to the interior diameter of the hole and, in some preferred embodiments, has locking protuberances, like threads, ridges, or barbs, that resist removal of the shaft from the hole in the bone when different types of forces, such as tensile or bending forces, are applied to the implant. The shaft is generally cylindrical in shape, however, in various embodiments of the invention, different cross-sections could be used. In a preferred embodiment of the present invention, the implant has a flattened and bent end portion emerging from only one side of the shaft. At the other side of the implant the outer surface of the shaft and the emerging end portion form a smooth surface, without any projections. This smooth surface at the end of the implant prevents irritation of the surrounding tissue. The end portion has a mating surface configured to grip a portion of the soft tissue surrounding the hole between the bone and the mating surface. The longitudinal axis of the shaft is oriented at an angle of less than 90 degrees relative to the mating surface. In this fashion, the implant anchors soft tissue, such as rotator cuff tissue, to bone.

Additional objects and features of the invention will be more readily apparent from the following detailed description and appended claims when taken in conjunction with the drawings.

DETAILED DESCRIPTION OF THE INVENTION

Figure 1:
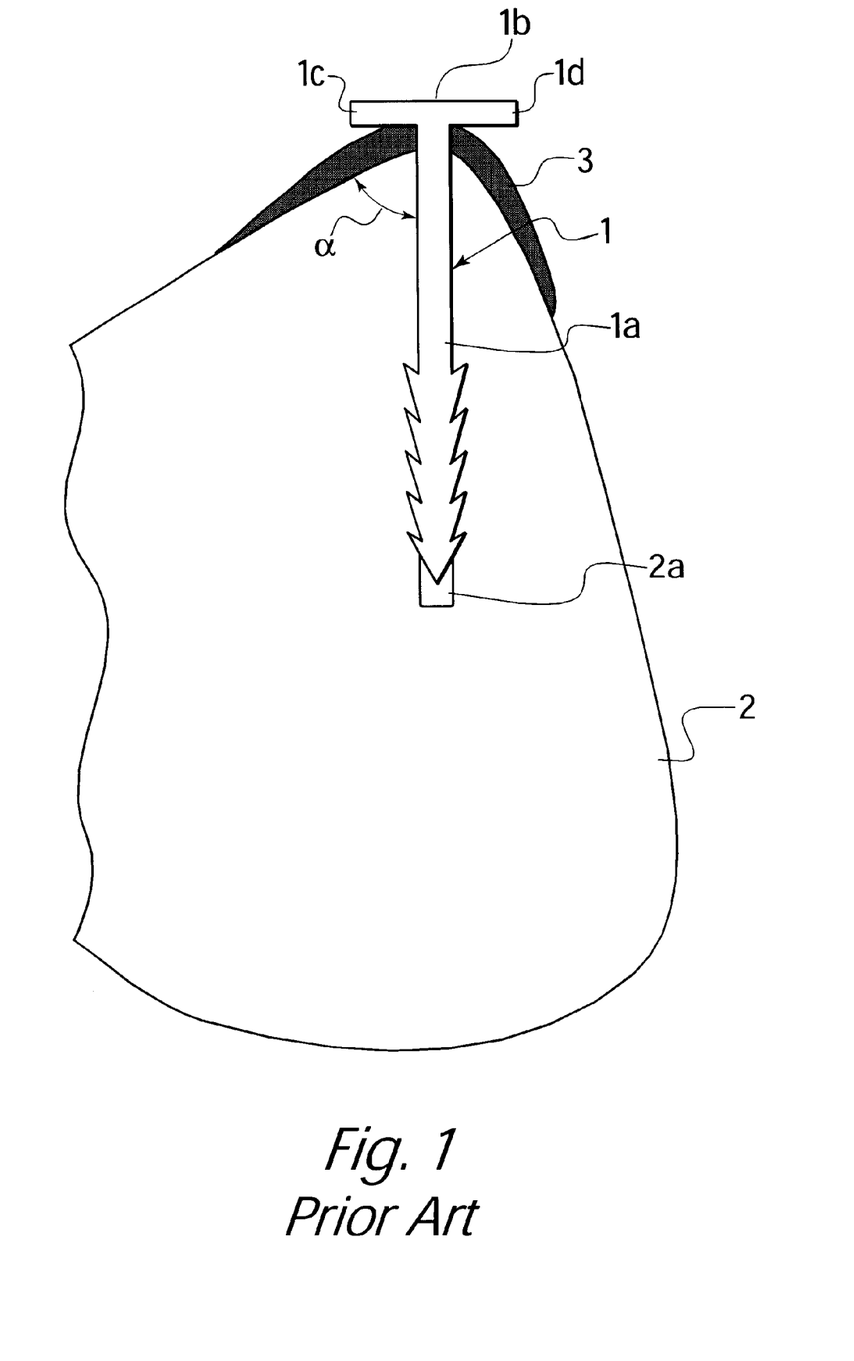
FIG. 1 is a schematic cross-sectional view of a prior art fixation implant (tack or screw) used in the fixation of soft tissue to a bone surface.

Reference is made to FIG. 1 wherein a prior art bioabsorbable implant (screw or tack) 1 is depicted. This implant comprises a shaft 1a and a symmetrical head 1b. The implant shaft 1a has been inserted into a drill hole 2a in bone 2 and the implant 1 fixes soft tissue 3 onto the surface of bone 2 around the shaft 1a and below the head 1b. The implant 1 has a conventional symmetrical head 1b whose diameter is larger than the diameter of the shaft 1a. The physiological forces, which tend to pull the soft tissue away from its fixed position, are directed to the right in FIG. 1. Therefore, only the left part 1c of head 1b in FIG. 1 effectively holds the soft tissue in place; the right part 1d of head 1b has no beneficial effect on the fixation of the soft tissue. Indeed, the right part 1d of the head 1b may cause harm by irritating nearby tissues inside of the shoulder joint. As can be seen from FIG. 1, the bottom mating surface of the prior art implant does not have good contact with the soft tissue to be treated. This is because the bottom mating surface of the implant is at right angles to the shaft of the implant, but the angle between the bone surface surrounding the hole and the shaft of the implant is less than 90°.

Figure 2A:
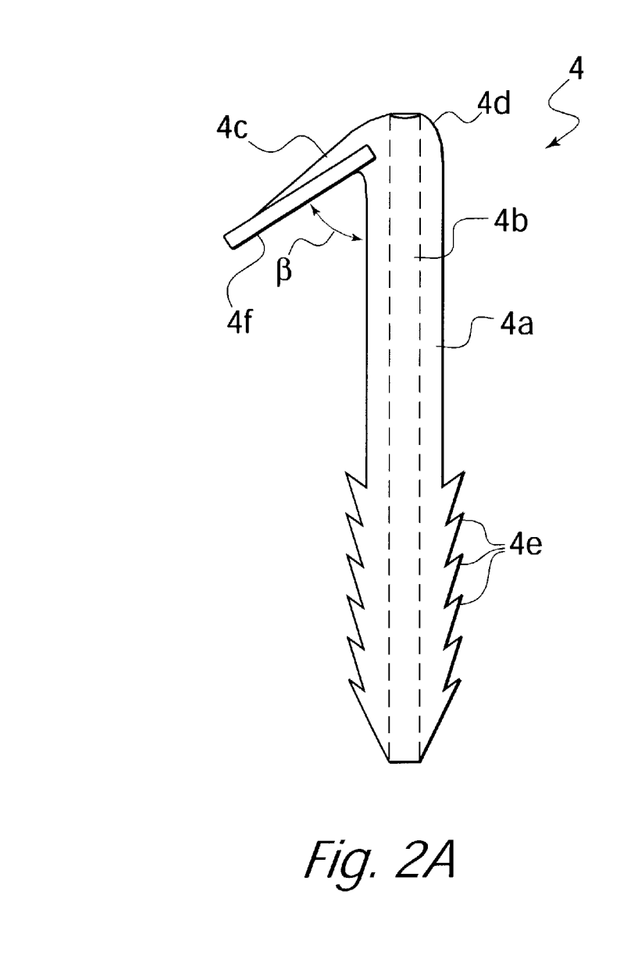
FIG. 2A and FIG. 2B are schematic front and side views, respectively, of a fixation implant in accordance with this invention.
Figure 2B:
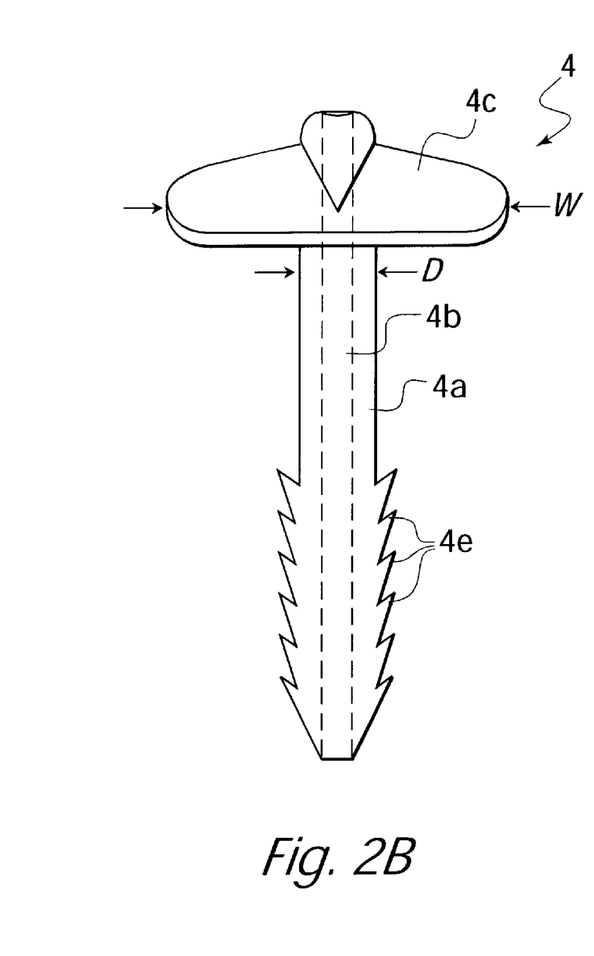

FIG. 2A and FIG. 2B portray a side and front view, respectively, of an embodiment of a bioabsorbable implant 4 of the invention. The implant has an elongated shaft portion 4a, preferably equipped with protuberances 4e, like threads, ridges, or barbs. In one embodiment of the invention, the shaft 4a is cannulated, i.e., contains a longitudinal hole, 4b. Such cannulation aids arthroscopic insertion. The implant 4 has a flattened and bent end portion 4c emerging from only one side of the shaft 4a so that at the other side of the shaft 4a the outer surface of the shaft 4a and the emerging end portion 4c form a smooth surface 4d. The flattened mating surface 4f of the end 4c is oriented at an angle β less than 90° with respect to the longitudinal axis of the shaft 4a. In various embodiments, the maximum width w of the end portion 4c can be larger, equal or smaller than the diameter d of the core of the shaft portion 4a.

Figure 2C:
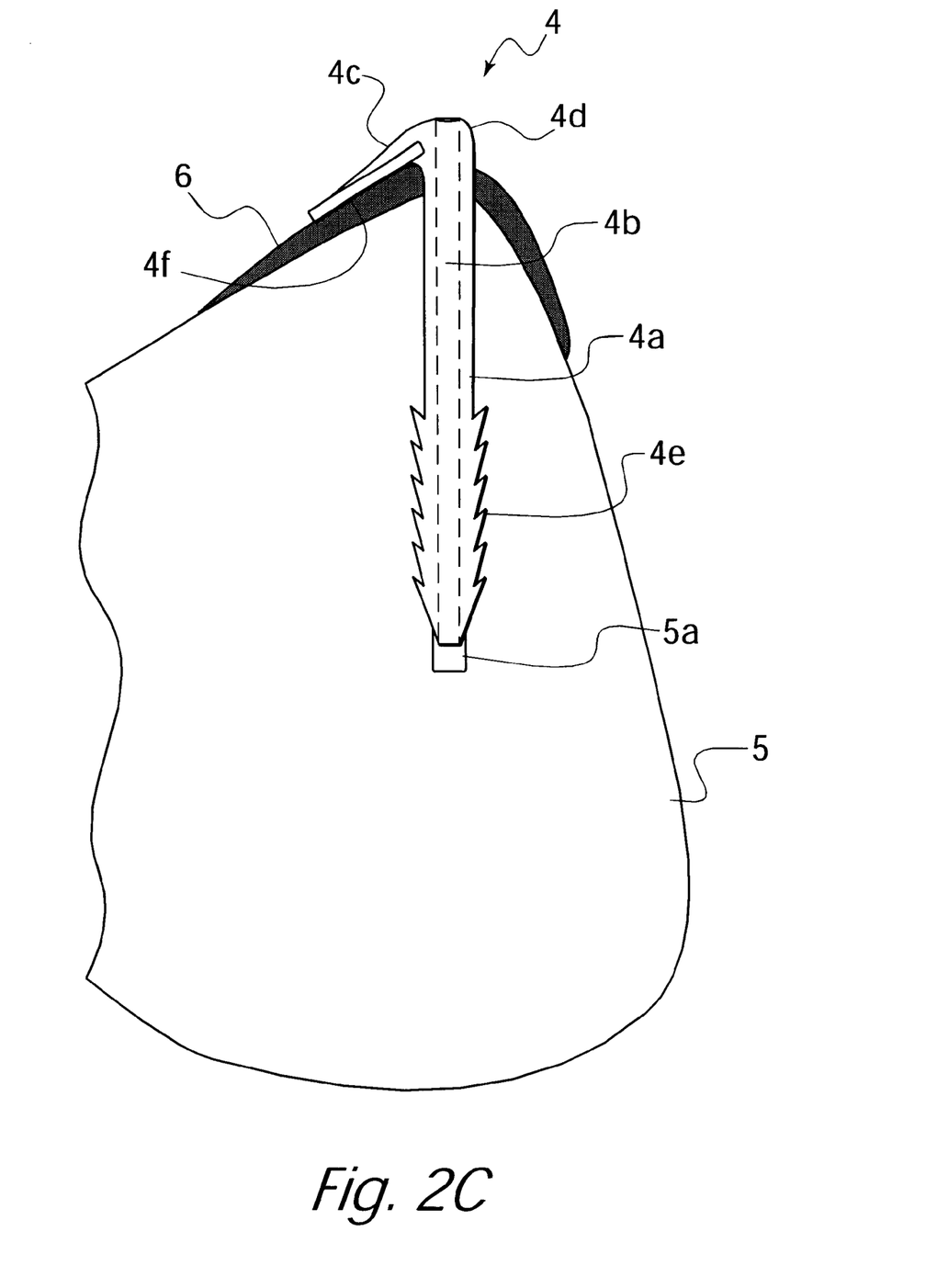
FIG. 2C is a schematic cross-sectional view of a fixation implant in accordance with this invention used in the fixation of soft tissue to a bone surface.
Figure 3:
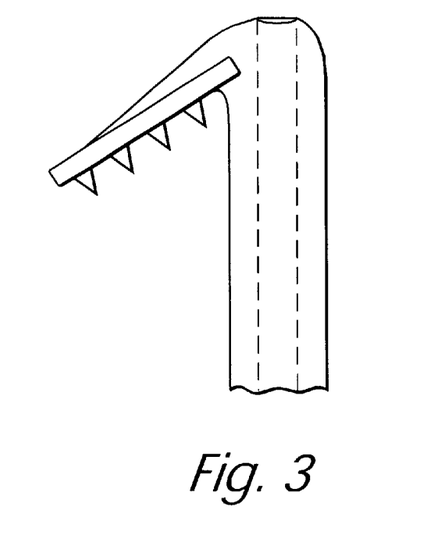
FIG. 3 is an enlarged schematic cross-sectional view of the end portion of a fixation implant in accordance with this invention showing spike-like protrusions on the lower mating surface of the implant.

As shown in FIG. 2C, the bioabsorbable implant 4 of the invention is inserted into a drill hole 5a in a bone 5. The implant 4 secures soft tissue 6 onto the surface of the bone 5 around the hole 5a and below the end portion 4c. To ensure that the implant is securely positioned in hole 5a, the shaft 4a has a maximum width greater than the interior diameter of said drill hole 5a in bone 5. At one side of the implant 4 the outer surface of the shaft 4a curves smoothly to the top of the implant. This smooth-surfaced area, 4d, has no projections and will not, therefore, irritate any surrounding tissue. The end portion 4c has a mating surface 4f configured to grip a portion of soft tissue 6 around said hole 5a between the bone 5 and the end 4c. The longitudinal axis of the shaft 4a is oriented at an angle of less than 90 degrees relative to the mating surface 4f. The shaft may have a longitudinal hole 4b inside of it. Such cannulated implants are especially advantageous because they can be inserted into a drill hole along a guide wire, with minimally invasive, arthroscopic surgical techniques.

In a preferred embodiment, the bioabsorbable implants of this invention are manufactured of bioabsorbable polymers, copolymers or polymer mixtures or alloys. This can be achieved with melt molding methods known in the prior art. It is also possible to use the techniques of U.S. Pat. No. 4,743,257, the entire disclosure of which is incorporated herein by reference, to mold absorbable fibers and binding polymer together in a compression or injection mold to create a fiber-reinforced or, preferably, a self-reinforced structure. The implants of this invention can be molded in a single compression molding cycle. The molding can be done, e.g., with an injection molding technique by injecting polymer melt into a mold cavity, which has the form of the implant of the invention, and by cooling the mold so that the molded implant solidifies and can be removed from the mold. The mold cavity may include a variety of reinforcement elements, such as a reinforcing fiber bundle, cord, fabric, etc. or short or long individual reinforcing fibers. Any protrusions on the surface of the shaft can be formed within a mold cavity or can be machined on the surface of the implant after the molding cycle.

The oriented or self-reinforced structure of the implants of the present invention can also be created by extruding or injection molding absorbable polymeric melt through a suitable die or into a suitable mold at high speed and pressure. When cooling occurs at suitable conditions, the flow orientation of the melt remains in the solid material as an oriented or self-reinforcing structure. In an advantageous embodiment, the mold can have the form of the implant, but it is also possible to manufacture the implants of the invention by machining and bending (possibly using heat) injection-molded or extruded semifinished products.

It is also advantageous to make the implants of meltmolded, solid state drawn or compressed, bioabsorbable polymeric materials, which are described, e.g., in U.S. Pat. Nos. 4,968,317 or 4,898,186, the entire disclosures of which are incorporated herein by way of this reference.

The reinforcing fibers of the implant can also be ceramic fibers, like bioabsorbable hydroxyapatite or bioactive glass fibers. Such bioabsorbable, ceramic fiber reinforced materials are described, e.g., in European Patent Application No. 0146398 and in WO 96/21628, the entire disclosures of which are incorporated herein by way of this reference.

The oriented or self-reinforced or otherwise fiber-reinforced implants of this invention can be manufactured by molding the reinforcement fiber-polymer matrix to the final product in a mold, whose mold cavity has the form of the final product. Alternatively, the final form can be machined mechanically (possibly also using heat) on a preform, such as a melt-molded and solid-state drawn rod, as is described, e.g., in U.S. Pat. No. 4,968,317.

Figure 4A:
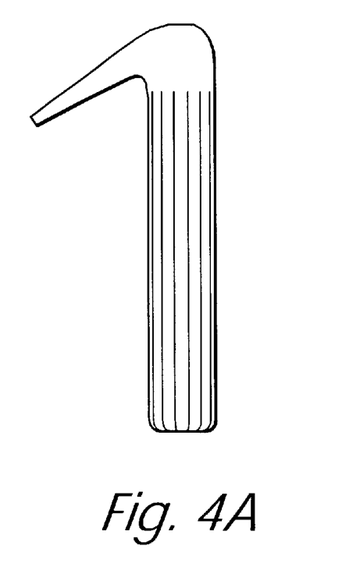
FIGS. 4A–4E are enlarged longitudinal cross-sectional views of the implants of the invention showing some preferred directions of molecular orientation and/or reinforcing elements.
Figure 4B:
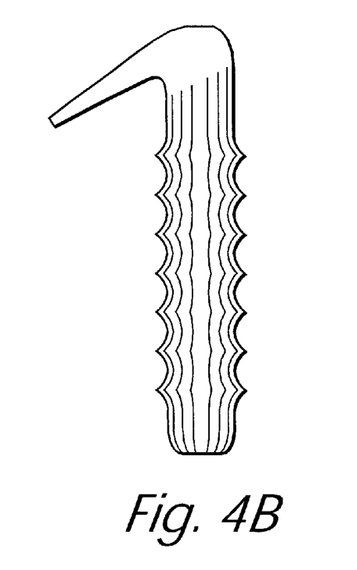
Figure 4C:
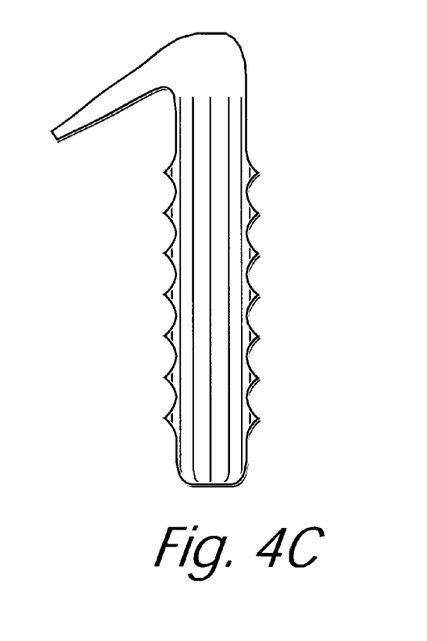
Figure 4D:
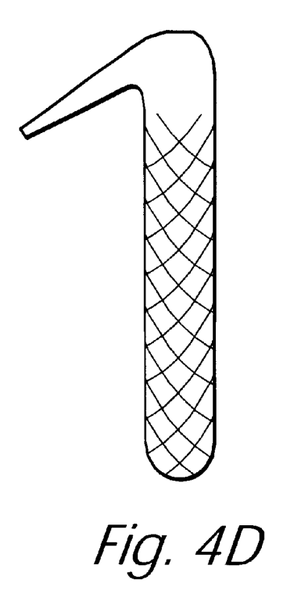
Figure 4E:
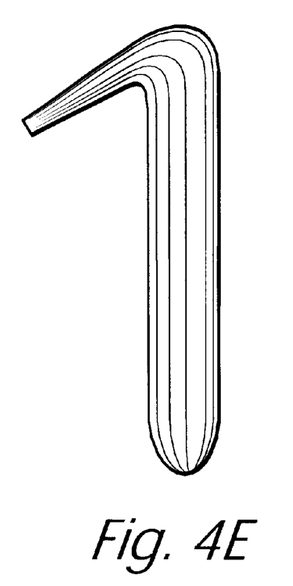

In some advantageous embodiments of this invention the orientation and/or reinforcing elements of the self-reinforced structure are mainly oriented in the direction of the long axis of the shaft of the implant (FIG. 4A) and may turn smoothly and continuously into the hook-like or hoe-like end portion, as is shown in the schematic cross-sectional FIG. 4E. The reinforcement elements may extend into any protrusions or ridges of the implant shaft (FIGS. 4B and 4C) and into any spikes of the end portion. In another embodiment of the present invention, the reinforcement elements turn spirally around the long axis of the implant (FIG. 4D). In addition, other different orientations of reinforcement elements in elongated samples, which are familiar from composite technology, can be applied to the present invention.

However, a general feature of orientation, fiber-reinforcement or self-reinforcement of the implants of this invention is that many of the reinforcing elements are oriented in such a way that they can carry effectively the different external loads (such as tensile, bending and shear loads) that are directed to the healing tissue (for example, loads to the shoulder joint caused by the movements of the muscles in the arm and/or in the upper part of patient's body).

According to an advantageous embodiment of the invention, the implant, or a special coating layer on its surface, may contain one or more bioactive substances, such as antibiotics, chemotherapeutic substances, angiogenic growth factors, substances accelerating the healing of the wound, growth hormones, and the like. Such bioactive implants are especially advantageous in surgical use, because they chemically contribute to the healing of the damaged tissue in addition to providing mechanical support.

The oriented and/or reinforced materials of the implants typically have tensile strengths of 100–2000 MPa, bending strengths of 100–600 MPa and shear strengths of 80–400 MPa. Additionally, they are usually stiff and tough. These mechanical properties are superior to those of non-reinforced absorbable polymers which typically show strengths between 40 and 100 MPa and are additionally either very flexible or brittle (see, e.g., Ref.: S. Vainionpää, P. Rokkanen and P. Törmälä, "Surgical Applications of Biodegradable Polymers in Human Tissues", Progr. Polym. Sci., 14, pp. 679–716 (1989), the entire disclosure of which is incorporated herein by way of this reference).

According to an advantageous embodiment of the invention, the end portion can be "overbended" in relation to the angle α between the mating surface of the bone and the drill hole in the bone. This means that the angle β of FIG. 2 is smaller than the anatomical angle α of FIG. 1. When the implant is pushed tightly into a drill hole in bone, angle β opens slightly to mate on the bone surface and a compression force is developed within the head of the implant. This compression is advantageous in securing the soft tissue to the bone.

The implants of the present invention may be sterilized by any of the well known sterilization techniques, depending on the type of material used to manufacture the implant. Suitable sterilization techniques include heat sterilization, radiation sterilization such as cobalt 60 or electron beam irradiation, ethylene oxide sterilization, and the like.

After the description above of the present invention and certain specific embodiments thereof, it will be readily apparent to those skilled in the art that many variations and modifications may be made to the present invention without departing from the spirit and scope thereof. The nonlimiting example below illustrates the production and properties of a certain embodiment of the implants of the present invention.

EXAMPLE 1

A single screw extruder was applied to manufacture a poly-L/DL-lactide (L/DL molar ratio 70/30, inh. viscosity 5.8 dl/g, trade name Resomer LR 708, manufacturer Boehringer Ingelheim, Germany) 8.6 mm thick cylindrical continuous billet, which was cooled to room temperature. The cooled billet was heated to 70° C. and it was drawn to the draw ratio of 3 according to PCT/FI 96/00511, Example 1, the entire disclosure of which is incorporated herein by way of this reference, to increase the strength and ductility of the material. The final oriented part had the diameter of 5 mm. The oriented part was cut into rods of 40 mm length. A hole of diameter 1.1 mm was drilled through the rods along the long axis of the rods. A 10 mm long segment at the end of the rods was located between two heated steel plates (T=80° C.) which were compressed to flatten the end of the rod to the thickness of 1 mm. At the same time the non-compressed part (shaft) of the rod was bent in relation to the flattened part so that an angle of 60° was formed between the mating surface of the flattened part and the long axis of the shaft. The drill hole inside of the shaft was opened by drilling through the hole inside the shaft and through the junction between the shaft and the end portion with a drill bit of 1.1 mm diameter.

Figure 5A:
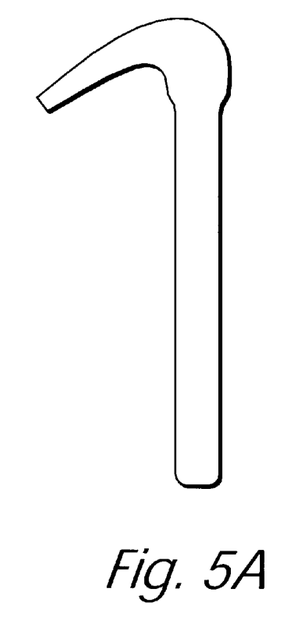
FIGS. 5A and 5B are longitudinal cross-sectional views of implants which can be drawn easily out of a drill hole in bone.
Figure 5B:
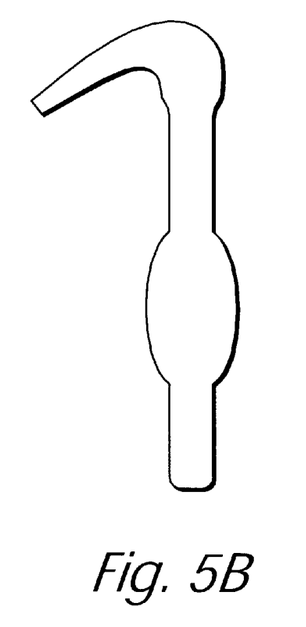
Figure 5C:
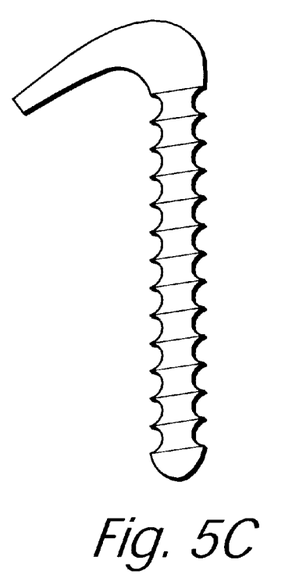
FIG. 5C is a longitudinal cross-sectional view of an implant of the invention which implant can be fixed strongly into a drillhole in bone.

The straight shafts of the implants were configured by lathing to the forms shown in FIGS. 5A–5C. In the case of FIG. 5A, the shaft was lathed to a smooth-surfaced, cylindrical form with a uniform diameter of 3.2 mm. In the case of FIG. 5B, the shaft was lathed to a smooth-surfaced cylindrical form with segments having a diameter of 3.2 mm at each end of the shaft and a 10 mm-long segment in the middle of the shaft having a diameter of 3.6 mm at its center that tapers to a diameter of 3.2 mm at each of its ends. In the case of FIG. 5C, the shaft was provided with threads by lathing the thread profile on the surface of the stem. The inner thread diameter was 3.2 mm and the outer thread diameter 3.6 mm. The distance between threads was 1 mm and the angle of inclination of the threads was 25°.

The fixation capacity of the above implants was tested with pull-out tests from bovine cancellous bone. Drill holes were made through the cortical bone into the cancellous bone in the distal part of a bovine femur bone with a drill bit of 3.2 mm diameter. The cortical part of the drill hole was widened with a 4.5 mm drill bit. The implants were tapped into the drill holes with a special tube-like applicator whose cross-section corresponded to the cross-section of the implant. A (1.5 mm thick) steel wire loop was left in the angle between the bent end and the shaft for the pull-out test. The implants were drawn out of the drill hole by fixing the steel wire loop into one jaw of a mechanical tensile testing machine and by fixing the bone to the other jaw. The maximum force to draw the implant out of the drill hole was measured. Six parallel samples were tested.

The pull-out force for the implants of FIG. 5A was 40±20 N, for implant of FIG. 5B 85±30 N and for the implants of FIG. 5C 170±40 N.

We claim:

1. A substantially bioabsorbable, one-piece implant for tissue fixation comprising: an elongated-cannulated shaft having a longitudinal axis and a first end, said first end having first and second sides, said first end comprising a mating surface projecting only from said first side of said elongated-cannulated shaft so that said second side of said first end of said elongate-cannulated shaft has a smooth surface without projection, said mating surface being oriented at an angle of less than 90 degrees with respect to said longitudinal axis of said shaft, and said mating surface having a width in a direction perpendicular to the longitudinal axis that is greater than the width of said shaft.

2. The implant of claim 1 wherein the outer surface of said elongated-cannulated shaft contains one or more protuberances.

3. The implant of claim 2 wherein the protuberances are barbs.

4. The implant of claim 2 wherein the protuberances are ridges.

5. The implant of claim 2 wherein the protuberances are screw threads.

6. The implant of claim 1 wherein the mating surface contains one or more protuberances.

7. The implant of claim 6 wherein the protuberances on the mating surface are spikes.

8. The implant of claim 1 wherein said implant comprises an oriented polymer.

9. The implant of claim 1 wherein said implant comprises a polymer containing reinforcement elements.

10. The implant of claim 1 wherein said implant comprises a self-reinforced polymer.

11. The implant of claim 1 wherein the implant has a pull-out strength in cancellous bone of at least 130 N.

12. The implant of claim 1 wherein said mating surface is substantially flat.

13. The implant of claim 1 wherein said implant is an implant for affixing soft material within the rotator cuff of a mammal.

14. A substantially bioabsorbable, one-piece implant for tissue fixation comprising: an elongated- cannulated shaft having a longitudinal axis and a first end, said first end having first and second sides, said first end comprising a mating surface projecting only from said first side, said mating surface being oriented at an angle of less than 90 degrees with respect to said longitudinal axis of said shaft, said implant comprising a polymer containing reinforcement elements, said reinforcement elements being located at least in the portion of the implant projecting from the outer surface of said shaft to form said mating surface.

15. The implant of claim 14 wherein said mating surface contains one or more protuberances.

* * * * *

UNITED STATES PATENT AND TRADEMARK OFFICE
CERTIFICATE OF CORRECTION

PATENT NO.     : 6,296,641 B2
DATED          : October 2, 2001
INVENTOR(S)    : W. Burkhead et al.

It is certified that error appears in the above-identified patent and that said Letters Patent is hereby corrected as shown below:

<u>Title page,</u>
Item [57], ABSTRACT,
Line 10, "embodiment the" should be -- embodiment, the --

Signed and Sealed this

Twenty-third Day of July, 2002

*Attest:*

*Attesting Officer*

JAMES E. ROGAN
*Director of the United States Patent and Trademark Office*